United States Patent [19]

Mesek et al.

[11] 4,044,768
[45] Aug. 30, 1977

[54] DIAPER WITH SPLIT PUFF BONDED FACING

[75] Inventors: Frederick K. Mesek, Tinley Park; Virginia L. Repke, Oak Forest, both of Ill.

[73] Assignee: Johnson & Johnson, New Brunswick, N.J.

[21] Appl. No.: 660,607

[22] Filed: Feb. 23, 1976

[51] Int. Cl.² ............................................. A61F 13/16
[52] U.S. Cl. ..................................... 128/287; 128/284; 128/290 R
[58] Field of Search ................... 128/287, 289, 290 R, 128/290 W, 296, 286

[56] References Cited
U.S. PATENT DOCUMENTS

| | | | |
|---|---|---|---|
| 3,759,775 | 9/1973 | Shepherd | 156/78 |
| 3,837,343 | 9/1974 | Mesek | 128/287 |
| 3,838,694 | 10/1974 | Mesek | 128/287 |
| 3,938,522 | 2/1976 | Repke | 128/287 |
| 3,965,904 | 6/1976 | Mesek et al. | 128/284 |

Primary Examiner—Stephen C. Pellegrino

[57] ABSTRACT

A diaper is provided having a facing layer comprising a fibrous nonwoven web having an exceptionally low weight per unit area for its loft and stength characteristics. The facing layer is made from an air laid web of mixed long and short fibers by impregnating the web with a volatile liquid composition containing a binder, rapidly vaporizing the volatile portions of the composition to cause puffing of the web while setting the web in puffed condition by solidification of the binder and thereafter splitting the puffed web into portions of lesser thickness and utilizing at least one of said portions as said facing layer.

13 Claims, 5 Drawing Figures

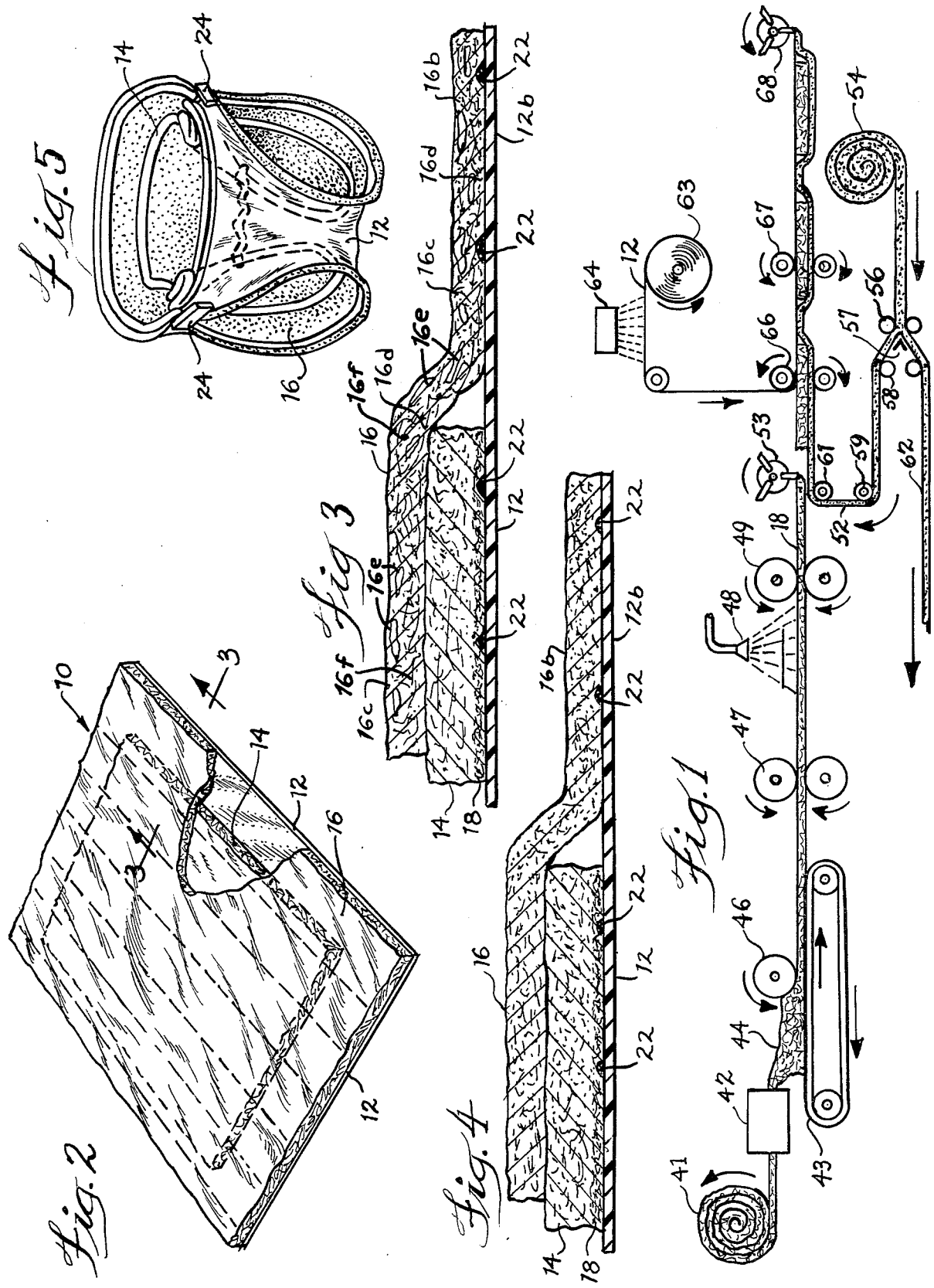

DIAPER WITH SPLIT PUFF BONDED FACING

BACKGROUND OF THE INVENTION

Disposable diapers have met with increased commercial acceptance in recent years primarily because of their convenience, as opposed to cloth diapers, which need to be laundered once soiled. Many different constructions have been proposed and used, and some have met with widespread commercial success in spite of certain inadequacies in functional properties.

One of the most serious prior art problems has been the inability to provide a suitable construction that would keep moisture away from the surface of the diaper which comes into contact with the infant's skin and thereby avoid skin irritation and infection. Commonly assigned Mesek et al. U.S. Pat. No. 3,612,055 discloses several diaper constructions that function extremely well in keeping moisture away from an infant's skin, while at the same time handling a full volume discharge of urine.

These functions are accomplished by a multilayer diaper comprising, in order, a fibrous facing layer which is to be brought into contact with the infant's skin, a layer of highly porous, loosely compacted cellulosic batt, a paper-like, densified, highly compacted cellulosic fibrous layer integral with the loosely compacted batt and an impervious backing sheet adhered to the densified layer throughout the interface therebetween. The facing layer is of porous construction and its fibers have less wettability for water than the fibers of the loosely compacted batt, resulting in a tendency for liquid to flow from the facing web into the batt. The densified fibrous layer has a smaller average pore size than the loosely compacted batt, resulting in a tendency for liquid to flow preferentially from the batt into the underlying densified layer rather than to other areas of the batt, thus tending to restrict wetting in the batt to an area of moderate size. Liquid flowing into the densified layer tends to spread laterally because of its wicking action and liquid which might pass through the densified layer during discharge (when flow is rapid) is held back by the impervious backing sheet for sufficient time to permit absorption to take place. Liquid in excess of the absorptive capacity of the densified layer is forced back by the impervious layer into the dry portion of the loosely compacted batt, thus utilizing the additional absorptive capacity therein.

The facing layer in the above-described diaper is comprised of a mixture of long and short fibers that are held together by a binder having a wetting agent therein which reduces the water repellency of the facing layer, so that urine may readily pass therethrough and into the loosely compacted batt. The facing layer, as described in the aforementioned patent is made by air laying a web of mixed long and short fibers, impregnating the web with a binder emulsion containing a wetting agent, and then drying the impregnated web.

It is desirable that the facing layer have a low density and high loft while retaining its strength but it has not been possible by the method described in U.S. Pat. No. 3,612,055 to produce facing layers having densities less than about 0.05 g./cc. It is also desirable, as a matter of minimizing diaper cost, to have a facing layer of low fabric weight, such as a weight of about 1½ oz./sq.yd.

Shepherd U.S. Pat. No. 3,759,775 describes a "puffed," or expanded web in which the fibers define strata, which, in turn, define fiber chambers larger than the expected interstitial spaces, which fiber chambers separate the fiber strata and act effectively as pores within the plane of the fabric. The fiber strata have a fiber density at or near that of conventionally laid dry fibers and the fiber chambers have a considerably lesser density.

The method described in U.S. Pat. No. 3,759,775 for making the expanded web involves impregnating a web with a vaporizable liquid which contains a binder in solution or emulsion and then rapidly vaporizing the volatile liquid to cause puffing of the web by entrapment of the generated vapors while setting the web in puffed condition by solidification of the binder.

A facing layer of high loft and low density can be made by the method of U.S. Pat. No. 3,759,775 from an air laid web of mixed long and short fibers. However, because the method of said patent requires entrapment of generated vapors within the web, there is a minimum web weight below which effective puffing is not achieved under practical conditions. It is not practical to puff a web weighing less than about 2 oz./sq.yd.; and facing layers at this weight are more costly than is desired in a competitively priced, disposable product.

SUMMARY OF THE INVENTION

The present invention provides an improved diaper having a facing layer which combines high loft, low density and low fabric weight. Specifically, the invention provides a multilayer diaper comprising: a water-repellent backing member; an absorbent batt positioned on one face of said backing member; and a facing layer in juxtaposed relationship with respect to said batt and said backing member, said facing layer comprising a nonwoven fibrous web including a randomly arranged, binder-stabilized, cellular, fibrous structure, said structure including chambers within the interior portion of the web surrounded by more dense fiber strata, and a binder interconnecting the fibers of said web, said binder being provided in sufficient quantity to prevent said fiber strata from collapsing, there being a density gradient between the opposite faces of said fibrous structure.

The facing layer in the above-described structure is made by impregnating an air laid web of mixed long and short fibers with a volatile liquid containing a binder dissolved or dispersed therein, then rapidly vaporizing the volatile liquid by applying heat substantially to an internal portion of the impregnated web at a rate sufficient to cause the expanding vapors of the volatile liquid to form fibrous membranes and to exert expansive forces on the membranes to separate portions of the web and produce a puffed web portion while setting, or solidifying, the binder while the fibers are in puffed condition to secure the fibers to one another at interconnections therebetween and thereby to define stable, enlarged interstices between the fibers, and finally splitting the thickness of the thus puffed web along at least one plane parallel to the web surfaces into at least two thickness portions and utilizing at least one of said thickness portions as the facing layer.

In the puffed web before splitting, produced as described above and as disclosed in more detail in the aforementioned U.S. Pat. No. 3,759,775, the stable enlarged interstices, or chambers, are larger in the midportion of the puffed web than at either surface. When the web is split into two thickness portions, each of the portions will retain one original outer surface with relatively small chambers and will have, at its opposite surface, a portion (which was an interior portion in the unsplit web) which has relatively large chambers. Thus, each thickness portion will have a density gradient between its opposite surfaces.

BRIEF DESCRIPTION OF THE DRAWINGS

FIG. 1 is a simplified schematic view of the production line on which the diaper is made;

FIG. 2 is a perspective view, with certain portions broken away for clarity of illustration, of an open, unfolded diaper;

FIG. 3 is an enlarged fragmentary cross-sectional view taken along line 3—3 of FIG. 2;

FIG. 4 is an enlarged fragmentary cross-sectional view similar to that of FIG. 3 but illustrating a different embodiment of the invention; and FIG. 5 is a perspective view on a reduced scale of the diaper of FIGS. 2 and 3 in its configuration after being put on an infant.

DETAILED DESCRIPTION OF THE INVENTION

Referring to the drawings, and particularly to FIGS. 2 and 3, the diaper assembly 10, when fully opened and laid out flat, comprises a lowermost water-impervious sheet 12 which is rectangular in shape, a highly water-absorbent fibrous pad, or batt 14, which is also rectangular in shape, but smaller than the impervious sheet and centrally disposed thereon, and an overlying facing layer 16 of fibrous material, which is also rectangular in shape, equal in dimension, and coterminous with the impervious sheet and in contact therewith in the marginal portions of the diaper extending peripherally beyond the absorbent pad, i.e., in the portions 16b and 12b of facing layer 16 and impervious sheet 12, respectively. The batt 14 has a paperlike densified highly compacted lowermost fibrous layer 18 which is adhered to the impervious sheet by bead lines of adhesive 22 substantially throughout the interface therebetween. Marginal portions 16b and 12b are also adhered to each other by head lines 22.

In the preferred embodiment of the invention, moisture-impervious sheet 12 is formed of polyethylene having a thickness of approximately 0.001 inch. The sheet may be smooth, or may be embossed to improve its drape and feel. Other suitable flexible moisture-impervious sheets may be used in accordance with the invention, such as, for example, polyethylene terephthalate sheets having a thickness of about 0.0005 inch.

Batt 14 is formed of loosely compacted short cellulose fibers, such as wood pulp fibers, or cotton linters, or mixtures thereof, which are primarily held together by interfiber bonds requiring no added adhesive, as is known in the art. Briefly, this batt is a low bulk density coherent web of loosely compacted cellulose fibers preferably comminuted wood pulp fibers in the form of so-called "fluff."

The term "short fibers," as used herein, refers to fibers less than about one-fourth inch in length, in contrast to "long fibers," or "textile length fibers" which are longer than about one-fourth inch in length, and generally are between about one-half and two inches in length. The former are substantially less costly than the latter. The classification of fibers by length may be carried out by the Clark Classification procedure described in the test manual of The Technical Association Of Pulp And Paper Industry (TAPPI-T233 SU64).

The paper-like densified layer 18 of batt 14 is formed by a slight moistening of one surface of the batt followed by the application of pressure thereto. The nature of the batt and of its densified layer and the method of producing the same are described in U.S. Pat. No. 3,017,304, dated Jan. 16, 1962.

The composite density of batt 14, including its densified layer 18, should be above about 0.07 gm./cc., and preferably between about 0.10 and 0.15 gm./cc. The foregoing density values are applicable to the diaper as produced. In storage and handling, the loft or thickness of the batt is increased to some extent, resulting in lowered densities.

Facing layer 16, as described in the above-mentioned application, is made up of a mixture of fibers consisting predominantly of short cellulosic fibers such as wood pulp fibers or cotton linters, in amounts of about 75 percent to about 98 percent, the balance being textile length fibers such as rayon. Short cellulosic fibers such as wood pulp fibers or cotton linters are substantially less expensive than textile length cellulosic fibers such as cotton and rayon, and this low cost is a factor in reducing the cost of the facing layer component of the diaper of this invention.

In the facing layer, the short fibers are in admixture with from about 2 to about 25 percent by weight of textile length fibers, such as 1.5 denier rayon fibers uniformly cut to 1½ inch length. In one embodiment of the invention the short and long fibers are substantially uniformly dispersed within the fiber strata so that fiber strata taken from different locations within the facing layer have substantially the same proportion of short and long fibers.

The fiber strata, as described above, and in the aforementioned U.S. Pat. No. 3,759,775, define fiber chambers larger than the expected interstitial spaces, which fiber chamber separate the fiber chambers and act effectively as pores within the plane of the fabric. The fiber strata have a density at or near that of conventionally laid dry fibers and the fiber chambers have a considerably lesser density.

The facing layer fabric is a coherent porous assembly of strata which interconnect with each other in a random fashion separating the fabric cross section into chambers, or macrovoids, which are interconnected within the plane of the fabric. In cross section transverse to the machine direction, the interconnected strata are generally substantially horizontal, although of wavy configuration. In cross section parallel to the machine direction, the interconnected strata are generally inclined to the plane of the fabric in the same general direction as the fibers in the original fabric (the "shingle" direction) although individual strata may vary from this direction.

The chambers, or macrovoids in the unsplit puffed web from which the facing layer is made are larger in the central thickness portion of the web than at either of its surfaces. After splitting along a plane parallel to the surfaces of the web, each newly created surface along the plane of the split will be in the vicinity of the larger chambers while the original external surfaces are still in the vicinity of the smaller chambers, resulting in a density gradient between opposite surfaces of the split fabric used as the facing layer.

Facing layers suitable for use in this invention have fabric weights less than about 3 oz./yd.$^2$ and preferably from about 1½ to about 2 oz./yd.$^2$. The density of the facing layers is less than 0.02 g./cc., and preferably from about 0.006 to about 0.015 g./cc.

An important aspect of this invention is the provision for selective wettability among the above-described fibrous components of the diaper and within the components themselves, such that the moisture is selectively drawn from the facing layer into the body of the batt and then from the body of the batt into the densified layer thereof.

In the diaper of this invention, as in the diaper of the aforementioned Mesek et al. U.S. Pat. No. 3,612,055, the least wettable of the fibrous elements is the facing layer. The wettability of the facing layer in the diaper of U.S. Pat. No. 3,612,055 is controlled by the balance of water-repellent binder and wetting agent deposited on the fibers of the web. The facing layer of this invention, because of its much lower density, has less wettability than the facing layer of the aforementioned Mesek et al. patent without in any way impairing its ability to permit urine to pass therethrough.

A useful parameter of wettability is the liquid-fiber contact angle for the individual fibers of the layer, the contact angle approaching 90° for fibers which are difficulty wettable, exceeding 90° for fibers which are highly water-repellent and approaching zero for fibers which are highly wettable by water. The liquid-fiber contact angle may be determined from interface high speed photographs of individual dry fibers, held in a clamp, and advanced into the wetting liquid (water) at a rate of 0.5 cm./sec. by techniques known in the art.

In any particular facing layer, the liquid-fiber contact angle for individual fibers may vary considerably because of unevenness of distribution of the water-repellent bonding agent and/or surfactant. Nevertheless, a liquid-fiber contact angle between about 30° and about 60° for most (over 50 percent) of the individual fibers in a random selection provides suitable wettability in the facing layer.

The body of batt 14 is substantially more wettable than the facing layer and tends to draw liquid away from the facing layer. The individual fibers of the batt are extremely wettable, generally having liquid-fiber contact angles below about 15° and approaching zero in the optimum embodiment. The wickability, or preferential absorptivity of the body of the batt for water is limited, however, by its low density which results in a large effective capillary radius for the capillaries between adjacent fibers.

The pressure causing a liquid to enter a cylindrical capillary is expressed by the equation:

$$P = (2\gamma \cos \theta)/r$$

where P is the capillary pressure, $\gamma$ is the surface tension of the liquid, $\theta$ is the liquid-fiber contact angle, and r is the capillary radius.

With a given liquid, the pressure (capillary force) increases with the cosine of the liquid-fiber contact angle (reaching a maximum where the angle is zero), and decreases with narrower capillary radii so that narrower capillaries will draw liquid from wider ones.

The relative wickability between facing layer 16 and the body of batt 14 is affected by both the relative densities of the layers and the relative wettability of the individual fibers in each layer. In an unpuffed facing layer of the type employed in the diaper described in Mesek et al. U.S. Pat. No. 3,612,055, the facing layer is somewhat more dense than the body of the batt but this difference is outweighed by the fact that the individual fibers of the batt have substantially lower liquid-fiber contact angles than those of the facing layer. This difference in fiber wettability overcomes the density difference between the two layers and provides a substantial net overall increase in capillary pressure to absorb liquid into the body of the batt.

In the present invention, the density of the facing layer is usually less than that of the batt and thus reinforces the difference in individual fiber wettability between the two layers and enhancing the wickability of aqueous liquids into the batt from the facing layer. This provides greater assurance that liquid will pass quickly through the facing layer into the batt and will not return to the facing layer.

In the embodiment of FIG. 3, the facing layer is disposed so that its large void side 16c (containing voids 16e and fiber strata 16f there-between and corresponding to the interior of the puffed web prior to splitting) faces outwardly and its small void side 16d lies against batt 14 and water-impervious sheet 12. In this embodiment, the density gradient within the facing layer reinforces the wickability gradient between the facing layer and the body of the batt and provides reassurance that whatever liquid may return to the facing layer after the batt is saturated will tend to stay in the layer closest to the batt and away from the baby's skin.

A disadvantage of the embodiment of FIG. 3, however, is that the facing layer in this embodiment tends to have low abrasion resistance in layer 16c.

In the embodiment of FIG. 4, the facing layer is disposed so that its small void side 16d (the exterior of the puffed web prior to splitting) faces outwardly and its large void side lies against batt 14 and water-impervious sheet 12. In this embodiment, the outer surface of the facing layer has excellent abrasion resistance. The density gradient within the facing layer in this embodiment would tend to concentrate liquid against the skin of the infant but the wickability gradient between the batt and the facing layer is so great that very little liquid flows back into the facing layer until the batt is heavily saturated. For most uses, the wickability characteristics of the embodiment of FIG. 4 are more than adequate and it may be selected for its excellent surface abrasion resistance characteristics.

In one form of the invention, as illustrated in FIG. 5, the diaper is provided with adhesive tabs 24, each having a fixed end secured to the impervious sheet 12 and a free end wherein the adhesive surface is covered with a facing sheet. The facing sheets are removed to expose the adhesive surfaces when the diaper is applied to the infant, as in the configuration shown in FIG. 5, and the free ends of the adhesive tabs are secured to opposite corners of the diaper.

In the embodiment discussed above, densified layer 18 is a continuous layer covering one entire face of batt 14. However, the densified layer may, if desired, be a widely distributed discontinuous layer, such as in the form of parallel, narrow densified strips running lengthwise of the diaper and separated by narrow undensified strips. Alternatively, the densified layer may be in the form of a rectangular grillwork of densified material encompassing a plurality of small areas of undensified material. Densified layers of this latter type are made in the same manner as the continuous densified layers described above, except that the compression is applied by embossed rollers, as described in the aforementioned U.S. Pat. No. 3,017,304.

Suitable fibrous structures for making the pads or batts 14 used in this invention are made from short cellusosic fibers obtained by the grinding or comminution of compacted wood pulp fibers or cotton linters. The compacted cellulosic material is at a moisture content of 5–10 weight percent (or is slightly moistened to bring it to that range) before being subjected to the grinding operation so that the fibers produced by grinding have sufficient moisture to have the capability of developing weak interfiber hydrogen bonds which give some coherence to the body of the batt.

The batts are initially formed by air blowing the slightly moist cellulosic fibers onto a support at a total weight of about 2 to about 10 oz./yd.$^2$, and then subjecting the air blown fibers to heavy compression. The small amount of moisture which may, when required, be added to cellulosic pulpboard is uniformly distributed throughout the air blown fibers by the grinding and air blow blown and after compression, this moisture provides weak hydrogen bonding to give some integrity to the body of the batt.

The dense compacted paper-like layer or skin is prepared by moistening a surface of the cellulosic batt with a fine spray of water, and then subjecting the moistened batt to pressure. The formation of the densified skin on the cellulosic batt is believed to be due to the formation of strong hydrogen bonds between contacting moistened fibers, similar to the bonds between the fibers in paper. By the proper selection of the amount of moisture applied to the surface of the batt and by the proper selection of degree of compresseion compression the properties of the densified skin may be varied as desired. The thickness, density, strength and other characteristics of the densified skin will depend upon the uniformity by which the moisture is applied, the depth to which it penetrates, and the degree to which the fibers are compressed. For example, by finely spraying about 0.0015 cc of H$_2$O/cm.$^2$ of web surface and then exposing the web to a pressure of about 40 lbs./in.$^2$, a suitable, densified, coherent paper-like skin 18 is obtained on the surface of the web which has been moistened.

The short fibers used in making batts 14 of this invention are generally entirely fibers of wood pulp or cotton linters. However, other cellulosic fibers may be used as well as blends of cellulosic fibers with other fibers such as silk, wool, nylon and cellulosic acetate. Highly purified kraft paper pulp fibers have proven to be most satisfactory for most applications.

The diaper of this invention may be assembled in equipment such as that schematically shown in FIG. 1. A roll of compacted wood pulp 41 is provided to feed a source of short cellulosic fibers to grinding mill 42 from which a stream of fibers is blown onto belt 43 as a layer 44 weighing between about 2 and about 10 oz./yd.$^2$ The pulpboard normally has a moisture content of 5 to 10 weight percent, but if it is lower (as from prolonged exposure to a dry atmosphere) the pulpboard is slightly moistened before grinding in mill 42 to bring its moisture content within the desired range.

Mill 42 grinds the pulpboard into individual short fibers. However, in one preferred embodiment, some of the pulpboard fibers are not completely comminuted and remain joined to other fibers in small clumps, generally smaller than about one-fourth inch across. It has been found that the presence of such small clumps of fibers in the body of batt 14 provides islands of increased tenacity for holding liquid. When an infant's weight on one portion of the batt densifies that portion and tends to concentrate the liquid in the densified portion, the presence of clumps of fibers elsewhere in the batt tends to hold the liquid in place. Preferably from about 2 to about 10 weight percent of the fibers should be in the form of such clumps.

The air blown layer is passed under compacting roll 46 from which it emerges with enough integrity to sustain itself as a web without the support of belt 43. The web then passes through a pair of calendar rolls 47 for further compression and then under nozzle 48 which deposits a fine spray of moisture on the upper surface of the web. The moistened web then passes between another set of calendar rolls 49 which exert heavy pressure to form a skin 51 on its upper surface.

The amount of moisture applied to the web may vary suitably from about 0.0005 to about 0.03 cc. of H$_2$O/cm.$^2$ of web surface, depending on the thickness of the web and the thickness of the paper-like densified skin desired, with lesser amounts of moisture being used for thinner webs and very thin, papery skins and greater amounts for thicker webs and skins of greater thickness.

The amount of pressure applied by rolls 49 may vary from about 4 to about 100 or more lbs./in.$^2$, with the commercially preferable range being from about 10 to about 50 lbs./in.$^2$ In a typical embodiment, the web is sprayed with about 0.0015 cc. of H$_2$O/cm.$^2$ of web surface and subjected to a pressure of about 40 lbs./in.$^2$ to obtain a densified, coherent papery skin on the surface of the web which has been moistened.

In the absorbent web and in the batts cut therefrom, there are weak hydrogen bonds in the body of the batt providing sufficient strength to maintain the integrity of the batt in ordinary handling, and there are strong hydrogen bonds in the densified layer or skin to increase the cohesive strength of the composite. After the skin is formed, the absorbent web comes into contact with a web of facing material 52 and is supported thereby while being cut by cutter 53 into individual batts 14.

Facing 52 is obtained from a roll 54 of a through-bonded, high loft, low density, puffed web made as described in the aforementioned Shepherd U.S. Pat. No. 3,759,775, which is hereby incorporated herein by reference.

Specifically, the method comprises providing a nonwoven fibrous web, impregnating the web with a vaporizable liquid, such as water, and a binder capable of securing the intersecting fibers together, vaporizing the liquid internally of at least portions of the web at a sufficiently faster rate than the rate at which the vapor can escape outward between the fibers and from the web to puff and expand at least portions of the web, and stabilizing these portions by setting the binder while the fibers are in a puffed condition. The degree of puffing may be closely controlled by controlling the rate of vaporization and vapor escape through the fibers and from the web and it is possible to puff a web to almost any degree and thus increase its thickness by 1% or less of its original thickness up to 10 times or more its original thickness and to stabilize the fibers in this exploded or puffed condition.

The product is essentially fibers having a small amount of binder for interconnecting the fibers in an expanded condition to provide high absorbency and low density. The puffed portion of the fibrous products prepared according to a preferred embodiment of this method essentially comprises longitudinally and transversely extending haphazardly arranged fibers. Carded webs or partially oriented webs of nonwoven fibers may also be used provided they are so disposed that the volatile liquid can operate effectively in the fiber structure. The fibers tend to define strata which, in turn, define fiber chambers larger than the expected interstitial spaces, fibers chambers separating the fiber strata and acting effectively as pores within the plane of the fabric, the fiber strata having a fiber density at or near that of conventionally laid dry fibers and the fiber chambers having a considerably less dense fiber density.

A particularly suitable manner of preparing a puffed web comprises providing a nonwoven fibrous web at least a portion of which contains both a small amount of binder and a substantial quantity of vaporizable liquid. The binder is activated, that is, made adhesive, if necessary and the vaporizable liquid is heated rapidly internally of the web to explosively vaporize the same and to puff the previously impregnated portion of the web to an expanded though structurally weak, low density portion. The binder is then deactivated or set while the previously impregnated portion of the web is in its puffed or expanded state. This secures the fibers together where they intersect and provides substantial structural integrity. The term "vaporizable liquid" contemplates a liquid capable of generating gases at a very rapid rate at temperatures which can be tolerated by the common synthetic and natural fibers. It is preferred that the liquid have a relatively low surface tension so that it will tend to adhere to the fibers as it partially is vaporized, thus forming discrete, rapidly expanding bubbles of vapor or walls interconnecting the fibers. It is further thought the bubbles cannot immediately escape from the web where the interfiber membranes extend during the explosive action. Therefore, the gases expand more or less in situ until the bubbles or membranes release the vapor entrapped therein, which then rapidly escapes through and from the web. The more rapid the vaporization, the greater will be the number of these expanding bubbles thrust into a given interstitial volume within the web at a given moment. It is thought that if the total volume of these expanding bubbles in a given interstitial portion at any moment is greater than the interstital volume of that web portion, that web portion expands, or becomes puffed in an explosive manner.

To rapidly vaporize the liquid, dielectric heating means are preferably used because of the speed of the action and the internal nature of the heating. Dielectric heating occurs generally through the absorption of electrical energy in a dielectric material exposed to a rapidly changing electromagnetic field. Thus, when using dielectric heating means, generally only dielectric substances having a substantial loss factor within the web absorb electrical energy and are heated directly. The heat generated in the fibrous web and the fluids held in the web depends upon the frequency of the electromagnetic field applied to the product, the applied voltage, the effective capacitance of the plates and dielectric material and the power factor or loss factor of the web. The power dissipated in the fiber web can be calculated in watts from the equation:

$$W = \frac{2\pi C E^2 (PF)}{10^6}$$

where
$\pi$ = frequency in Hertz
C = capacitance in microfarads
E = applied r.m.s. voltage
PF = power factor The dielectric liquid throughout the web will be rapidly heated fairly uniformly according to this equation rather than being heated much more slowly from the outside inwardly as is the case with conventional steam, hot air, or infrared dryers.

During heating and drying of webs, most binders which are solvent activated, tend to migrate somewhat toward the surface of the web especially if the binder pick-up weight is relatively high; and, therefore, the surface adjacent portions of the web will have a higher binder content than the center portions of the web. As a result, a relatively hard "skin" may be formed on the web surfaces. The web portions interposed between the surface adjacent portions tend to be less dense and remain softer and somewhat springy, and these portions are at an outer surface of the puffed web after it is split in thickness in accordance with this invention.

The amount of binder in the puffed web should be selected to provide the desired interfiber bonds while maintaining the absorbent interstices. In the preferred embodiments, the binder comprises less than about 10% and most preferably between about 4% and 7% of the fabric, by weight on a dry solids basis and with this amount, there is an optimum structural stability and minimum tendency to collapse while still maintaining lightweight and high absorbency. Binder add-on in the range of about 1% to about 30% of dry solids by weight can be used. The lower range is acceptable where increased structural collapse under compression is not excessively detrimental, and the upper range is useful where increased rigidity is desired although some increase in cost and weight and some decrease in absorptive capacity may be detected.

As the puffed web is unwound from roll 54, it passes between rolls 56 before being split in thickness by wedge 57. Facing 52, comprising one thickness portion of the puffed web passes over rolls 58, 59 and 61 to join the absorbent web as described above while thickness portion 62 is passed to a similar diaper assembly line, or is rolled up for storage.

Polyethylene film 12 is fed to the assembly from roll 63, lines of adhesive being applied from the applicator 64. As described above, the adhesive is applied as parallel lines or beads between the impervious sheet and the densified layer of the batt (or the facing layer in the marginal portion of the diaper). Adhesive may, if desired, be applied as a continuous layer between the polyethylene and the batt, but such application tends to provide excessive stiffness. The adhesive may also be applied in other patterns, such as spaced dots or other forms of so-called "island" bonds, but fairly close overall adhesion between the sheet and the batt is required and no portion of the polyethylene should be more than about 2 inches from a point of adhesion. In the absence of such close overall adhesion, the polyethylene film may be separated from the densified layer to create substantial space in which uncontrollably large amounts of free liquid urine can accumulate.

After the facing material and polyethylene are brought into contact with opposite faces of the absorbent batts, the assembly is subjected to compression by rolls 66 and 67 to shape the diaper assembly, and the individual diapers are cut off by cutter 68.

It will be understood by those skilled in the art that variations and modifications of the specific embodiments described above may be employed without departing from the scope of the invention as defined in the appended claims.

We claim:

1. A multi-layer diaper comprising: a water-repellent backing member; an absorbent batt positioned on one face of said backing member; and a facing layer in juxtaposed relationship with respect to said batt and said backing member, said facing layer comprising a nonwoven fibrous web including a randomly arranged, binder-stabilized, cellular, fibrous structure, said structure including chambers within the interior portion of the web surrounded by fiber strata more dense than the density within said chambers, and a binder interconnecting the fibers of said web, said binder being provided in sufficient quantity to prevent said fiber strata from collapsing, there being a density gradient between the opposite faces of said fibrous structure, the structure being more dense at one face than at the opposite face and having smaller chambers at one face than at the opposite face.

2. The diaper of claim 1 wherein said density gradient provides a least dense portion of said facing layer facing said backing layer and a most dense portion facing outwardly and being adapted to be positioned adjacent an infant's skin.

3. The diaper of claim 1 wherein said density gradient provides a most dense portion of said facing layer facing said backing layer and a least dense portion facing outwardly and being adapted to be positioned adjacent an infant's skin.

4. The diaper of claim 1 wherein at least some of the chambers in said facing layer are essentially devoid of fibers.

5. The diaper of claim 1 wherein said facing layer comprises predominantly short fibers having lengths less than about ¼ inch and a minor percentage of long fibers having lengths in excess of ½ inch.

6. The diaper of claim 1 wherein said long fibers comprise from about 2 to about 25 percent of said fibers by weight.

7. The diaper of claim 1 wherein said facing layer has an average density of less than about 0.02 gm./in.$^3$ 8. The diaper of claim 7 wherein the weight of the binder in said facing layer is in the range of about 1 percent to about 30 percent of the weight of the fabric on a dry solids basis.

9. The diaper of claim 8 wherein the weight of the binder in said facing layer is less than about 10 percent of the weight of the fabric on a dry solids basis.

10. The diaper of claim 9 wherein the weight of the binder in said facing layer is between about 4 percent and about 7 percent of the weight of the fabric on a dry solids basis.

11. The method of making a diaper comprising the steps of impregnating a nonwoven web of discrete fibers with a volatile liquid containing a binder capable of stabilizing said fibers as an interconnected web, rapidly vaporizing said volatile liquid by applying heat substantially to an internal portion of said impregnated web at a rate sufficient to cause expanding vaporized liquid to form liquid membranes within said web and to exert expensive forces on said liquid membranes between said fibers and to thereby separate portions of mid web and produce a puffed web portion, setting the binder material while said fibers are in the puffed condition to secure said fibers to one another at interconnections therebetween and thereby to produce a stabilized puffed web with a structure including chambers within the interior of the web surrounded by more dense fiber strata; and thereafter splitting said web into at least two thickness portions, bringing one face of one of said thickness portions into face to face contact with one face of an absorbent batt with areas of said thickness portion overlapping the edges of said batt, bringing an opposite face of said batt and said overlapping areas of said thickness portion into contact with an impervious flexible layer, and adhering said impervious flexible layer to said opposite face of said batt and to said overlapping areas of said thickness portion.

12. The method of claim 11 wherein said one face of said thickness portion is a face which was an external face of said stabilized puffed web before said splitting.

13. The method of claim 11 wherein said one face of said thickness portion is a face which was formed during said splitting step from an interior portion of said stabilized puffed web.

* * * * *